(12) United States Patent
August et al.

(10) Patent No.: US 7,608,407 B2
(45) Date of Patent: Oct. 27, 2009

(54) FLUORESCENCE POLARIZATION ASSAY FOR DETERMINING HISTIDINE DECARBOXYLASE ACTIVITY

(75) Inventors: E. Michael August, Southbury, CT (US); Daniel Rajotte, Quebec (CA)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 7 days.

(21) Appl. No.: 11/273,526

(22) Filed: Nov. 14, 2005

(65) Prior Publication Data

US 2006/0105404 A1 May 18, 2006

Related U.S. Application Data

(60) Provisional application No. 60/628,242, filed on Nov. 16, 2004.

(51) Int. Cl.
*G01N 33/53* (2006.01)
*G01N 33/543* (2006.01)

(52) U.S. Cl. .................. 435/7.1; 435/7.21; 435/7.4; 435/7.91; 435/7.94; 424/9.4; 436/501; 436/517

(58) Field of Classification Search .................. None
See application file for complete search history.

(56) References Cited

U.S. PATENT DOCUMENTS 6,297,361 B1 10/2001 Haak-Frendscho et al.

OTHER PUBLICATIONS

Tanimoto et al. (Pathology International, 2004, vol. 54, pp. 408-412).*
Molnar et al. (European Journal of Clinical Investigation, 2002, vol. 32, pp. 743-749).*
Dy et al. (Blood, vol. 87, No. 8, Apr. 15, 1996, pp. 3161-3169).*
The Pathcentre News, vol. 3, No. 2, Oct. 1997, p. 27.*
Kinoshita, E., et al. "Novel histamine measurement by HPLC analysis used to assay histidine decarboxylase inhibitory activity of shoyuflavones from soy sauce" Bioscience, Biotechnology, and Biochemistry, 1998 vol. 62, No. 8, pp. 1488-1491 XP002382521.
Owicki, J. C., et al. "Fluorescence Polarization and Anisotropy in High Throughput Screening: Perspectives and Primer" Journal of Biomolecular Screening, 2000, vol. 5, No. 5, pp. 297-306 XP009007612.
Burke, T. J., et al. "Development and Application of Fluorescence Polarization Assays in Drug Discovery" Current Topics in Medicinal Chemistry, 2003 vol. 6. No. 3, pp. 183-194 XP008050421.
Guesdon, J. L., et al. "Monoclonal anti-histamine antibody. Preparation, Characterization and application to enzyme immunoassay of histamine" Journal of Immunological Methods 1986, vol. 87, No. 1, pp. 69-78 XP002382522.
Kimihito Maeda, et al; Induction of L-Histidine Decarboxylase in a Human Mast Cell Line, HMC-1; Experimental Hematology (1998) vol. 26 pp. 325-331.
Marek Jutel et al; Immune Regulation by Histamine Opinion; Current Opinion in Immunology (2002) vol. 14 pp. 735-740.
Elke Schneider et al; Trends in Histamine Research: New Functions During Immune responses and Hematopoiesis; Trends in Immunology (2002) vol. 23, No. 5, pp. 255-263.
Kimio Yatsunami et al; Comparative Studies of Human Recombinant 74- and 54-kDa l-Histidine Decarboxylases; The Journal of Biological Chemistry (1995) vol. 270, No. 51, pp. 30813-30817.
Satoshi Tanaka et al; Degradation of the 74 kDa Form of l-Histidine Decarboxylase Via the Ubiquitin-Proteasome Pathway in a Rat Basophilic/Mast Cell Line (RBL-2H3); FEBS Letters (1997) vol. 417 pp. 203-207.
Hiroshi Ohtsu et al; New Functions of Histamine Found in Histidine Decarboxylase Gene knockout Mice; Biochemical and Biophysical Research Communications (2003) vol. 305 pp. 443-447.
Hiroshi Ohtsu et al; Mice Lacking Histine Decarboxylase Exhibit Abnormal Mast Cells; FEBS Letters (2001) vol. 502 pp. 53-56.
Gergely T. Kozma et al; Histamine Deficiency in Gene-Targeted Mice Strongly Reduces Antigen-Induced Airway Hyper-Responsiveness, Eosinophilia and Allergen-Specific IgE; International Immunology (2003) vol. 15, No. 8, pp. 963-973.
Hiroshi Ohtsu et al; Plasma Extravasation Induced by Dietary Supplemented Histamine-Free Mice: Eur. J. Immunol. (2002) vol. 32 pp. 1698-1708.
Ajoy Kumar Ghosh et al; Defective Angiogenesis in the Inflammatory granulation Tissue in Histidine Decarboxylase-deficient Mice but not in Mast Cell-Deficient Mice; J.Exp. Med. (2002) vol. 195, No. 8 pp. 973-982.
E. Masini et al; Histamine and Histidine Decarboxylase Up-Regulation in Colorectal Cancer: Correlation with Tumor Stage; Inflamm Res. (2005) vol. 54 Supplement 1 pp. S80-S81.
W.A. Fogel et al; Ornithine and Histidine Decarboxylase: Activites in Hypertrophic and Hyperplastic Mouse Kidney; Inflammation Research (2005) vol. 54 supplement 1 pp. S62-S63.
Philipp Christen et al; From Cofactor to enzymes. The Molecular Evolution of Pyridoxal-5'-Phosphate-Dependent Enzymes; The Chemical Record (2001) vol. 1 pp. 436-447.
J.-L. Guesdon et al; Monoclonal Anti-Histamine Antibody: Preparation, Characterization and Application to enzyme Immunoassay of Histamine; Journal of Immunology Methods (1986) vol. 87 pp. 69-78.

(Continued)

*Primary Examiner*—Lisa V Cook
(74) *Attorney, Agent, or Firm*—Michael P. Morris; Edouard G. Lebel; David A. Row

(57) ABSTRACT

The present invention relates to fluorescence polarization assays for determining the HDC modulating activity of a candidate compound including providing a reaction mixture comprising a HDC, histidine, a fluorescently labeled histamine probe, a candidate compound and an anti histamine antibody having selectivity for histamine at least 10 fold greater than histidine: incubating the reaction mixture; and determining whether inhibition of HDC has occurred in the presence of the test compound, wherein an increase in fluorescence signal is an indication that the test compound inhibits the activity of the HDC.

17 Claims, 7 Drawing Sheets

OTHER PUBLICATIONS

Takehiko Watanabe et al; Pharmacology of α-Fluoromethylhistidine, a Spedific Inhitor of Histidine Decarboxylase; TIPS (1990) vol. 11 pp. 363-367.

Akiko Watabe et al; Purification and Properties of $_L$-Histidine Decarboxylase from Mouse Stomach; Biochemical Pharmacology (1992) vol. 43, No. 3 pp. 587-593.

Hargita Hegyesi et al; Suppression of Melanoma Cell Proliferation by Histidine Decaroxylase Specific Antisense Oligonucleotides; Journal Investigative Dermatology (2001) vol. 117 pp. 151-153.

L. A. Fitzpatrick et al; Targeted Deletion of Histine Decarboxylase Gene in Mice Increases Bone Formation and Protects Against Ovariectome-Induced Bone Loss; PNAS (2003) vol. 100, No. 10 pp. 6027-6032.

K. Sieja et al; Concentration of histamine in Serum and Tissues of the Primary Ductal Breast Cancers in Women; The Breast (2005) vol. 14 pp. 236-241.

Robert Roskoski, Jr.; A Rapid Histidine Decarboxylase Assay; Analytical Biochemistry (1978) vol. 87 pp. 293-297.

* cited by examiner

A.

B.

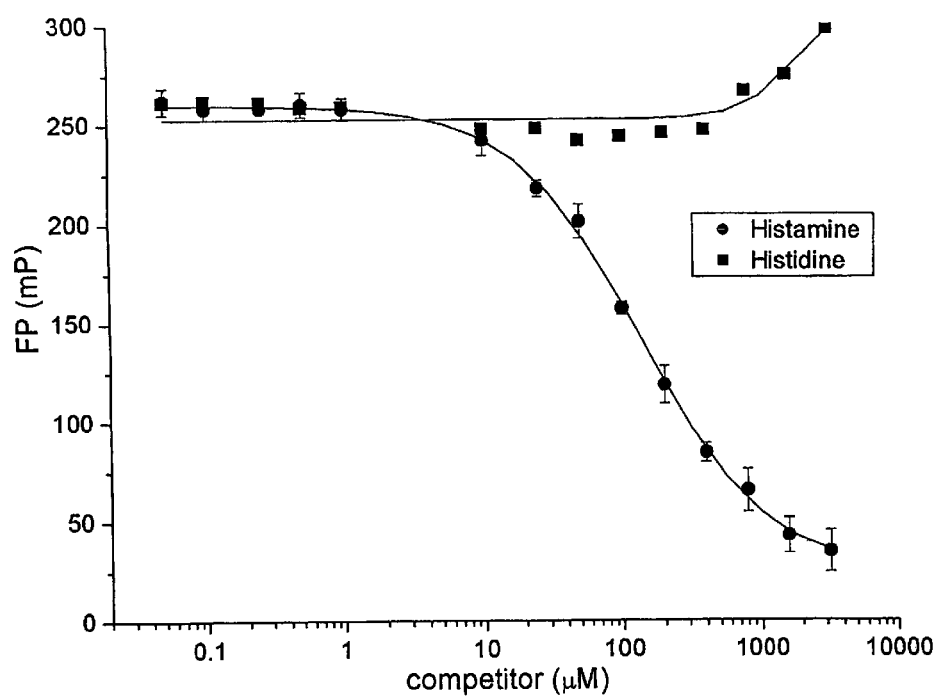

SEQUENCE LISTING

<160> NUMBER OF SEQ ID NOS: 1

<210> SEQ ID NO 1
<211> LENGTH: 662
<212> TYPE: PRT
<213> ORGANISM: Homo sapiens

<400> SEQUENCE: 1

Met Met Glu Pro Glu Glu Tyr Arg Glu Arg Gly Arg Glu Met Val Asp
1               5                   10                  15

Tyr Ile Cys Gln Tyr Leu Ser Thr Val Arg Glu Arg Arg Val Thr Pro
            20                  25                  30

Asp Val Gln Pro Gly Tyr Leu Arg Ala Gln Leu Pro Glu Ser Ala Pro

-continued

```
                35                  40                  45
Glu Asp Pro Asp Ser Trp Asp Ser Ile Phe Gly Asp Ile Glu Arg Ile
 50                  55                  60

Ile Met Pro Gly Val Val His Trp Gln Ser Pro His Met His Ala Tyr
 65                  70                  75                  80

Tyr Pro Ala Leu Thr Ser Trp Pro Ser Leu Leu Gly Asp Met Leu Ala
                 85                  90                  95

Asp Ala Ile Asn Cys Leu Gly Phe Thr Trp Ala Ser Ser Pro Ala Cys
                100                 105                 110

Thr Glu Leu Glu Met Asn Val Met Asp Trp Leu Ala Lys Met Leu Gly
                115                 120                 125

Leu Pro Glu His Phe Leu His His Pro Ser Ser Gln Gly Gly Gly
130                 135                 140

Val Leu Gln Gln Thr Val Ser Glu Ser Thr Leu Ile Ala Leu Leu Ala
145                 150                 155                 160

Ala Arg Lys Asn Lys Ile Leu Glu Met Lys Thr Ser Glu Pro Asp Ala
                165                 170                 175

Asp Glu Ser Cys Leu Asn Ala Arg Leu Val Ala Tyr Ala Ser Asp Gln
                180                 185                 190

Ala His Ser Ser Val Glu Lys Ala Gly Leu Ile Ser Leu Val Lys Met
                195                 200                 205

Lys Phe Leu Pro Val Asp Asp Asn Phe Ser Leu Arg Gly Glu Ala Leu
210                 215                 220

Gln Lys Ala Ile Glu Glu Asp Lys Gln Arg Gly Leu Val Pro Val Phe
225                 230                 235                 240

Val Cys Ala Thr Leu Gly Thr Thr Gly Val Cys Ala Phe Asp Cys Leu
                245                 250                 255

Ser Glu Leu Gly Pro Ile Cys Ala Arg Glu Gly Leu Trp Leu His Ile
                260                 265                 270

Asp Ala Ala Tyr Ala Gly Thr Ala Phe Leu Cys Pro Glu Phe Arg Gly
                275                 280                 285

Phe Leu Lys Gly Ile Glu Tyr Ala Asp Ser Phe Thr Phe Asn Pro Ser
290                 295                 300

Lys Trp Met Met Val His Phe Asp Cys Thr Gly Phe Trp Val Lys Asp
305                 310                 315                 320

Lys Tyr Lys Leu Gln Gln Thr Phe Ser Val Asn Pro Ile Tyr Leu Arg
                325                 330                 335

His Ala Asn Ser Gly Val Ala Thr Asp Phe Met His Trp Gln Ile Pro
                340                 345                 350

Leu Ser Arg Arg Phe Arg Ser Val Lys Leu Trp Phe Val Ile Arg Ser
                355                 360                 365

Phe Gly Val Lys Asn Leu Gln Ala His Val Arg His Gly Thr Glu Met
370                 375                 380

Ala Lys Tyr Phe Glu Ser Leu Val Arg Asn Asp Pro Ser Phe Glu Ile
385                 390                 395                 400

Pro Ala Lys Arg His Leu Gly Leu Val Val Phe Arg Leu Lys Gly Pro
                405                 410                 415

Asn Cys Leu Thr Glu Asn Val Leu Lys Glu Ile Ala Lys Ala Gly Arg
                420                 425                 430

Leu Phe Leu Ile Pro Ala Thr Ile Gln Asp Lys Leu Ile Ile Arg Phe
                435                 440                 445

Thr Val Thr Ser Gln Phe Thr Thr Arg Asp Asp Ile Leu Arg Asp Trp
450                 455                 460
```

-continued

```
Asn Leu Ile Arg Asp Ala Ala Thr Leu Ile Leu Ser Gln His Cys Thr
465                 470                 475                 480

Ser Gln Pro Ser Pro Arg Val Gly Asn Leu Ile Ser Gln Ile Arg Gly
                485                 490                 495

Ala Arg Ala Trp Ala Cys Gly Thr Ser Leu Gln Ser Val Ser Gly Ala
                500                 505                 510

Gly Asp Asp Pro Val Gln Ala Arg Lys Ile Ile Lys Gln Pro Gln Arg
            515                 520                 525

Val Gly Ala Gly Pro Met Lys Arg Glu Asn Gly Leu His Leu Glu Thr
        530                 535                 540

Leu Leu Asp Pro Val Asp Asp Cys Phe Ser Glu Glu Ala Pro Asp Ala
545                 550                 555                 560

Thr Lys His Lys Leu Ser Ser Phe Leu Phe Ser Tyr Leu Ser Val Gln
                565                 570                 575

Thr Lys Lys Lys Thr Val Arg Ser Leu Ser Cys Asn Ser Val Pro Val
            580                 585                 590

Ser Ala Gln Lys Pro Leu Pro Thr Glu Ala Ser Val Lys Asn Gly Gly
            595                 600                 605

Ser Ser Arg Val Arg Ile Phe Ser Arg Phe Pro Glu Asp Met Met Met
        610                 615                 620

Leu Lys Lys Ser Ala Phe Lys Lys Leu Ile Lys Phe Tyr Ser Val Pro
625                 630                 635                 640

Ser Phe Pro Glu Cys Ser Ser Gln Cys Gly Leu Gln Leu Pro Cys Cys
                645                 650                 655

Pro Leu Gln Ala Met Val
                660
```

FLUORESCENCE POLARIZATION ASSAY FOR DETERMINING HISTIDINE DECARBOXYLASE ACTIVITY

RELATED APPLICATIONS

This application claims the benefit of U.S. provisional application No. 60/628,242 filed Nov. 16, 2004 the contents of which are incorporated herein.

BACKGROUND OF THE INVENTION

1. Technical Field

The field of the invention relates to fluorescence polarization assays for detecting HDC activity that can be used in the diagnosis of disease and identification of HDC inhibitor agents.

2. Background Information

Histamine is a potent bioamine with multiple activities in various pathological and physiological conditions (Jutel M, Watanabe T, Akdis M, Blaser K, Akdis C A: Immune regulation by histamine. Curr. Opin. Immunol 2002; 14:735-740). In addition to its well-characterized effects on the acute inflammatory and allergic responses, histamine regulates several aspects of antigen-specific immune responses (Schneider E, Rolli-Derkinderen M, Arock M, Dy M: Trends in histamine research: new functions during immune responses and hematopoiesis. Trends Immunol 2002; 23:255-263). Recent findings, such as the discovery of a novel histamine receptor (H4) on immunocompetent cells and the demonstration of a role for H1 and H2 receptors on T helper cell polarization, have generated much interest in the immune-regulatory mechanisms triggered by histamine (Schneider E, Rolli-Derkinderen M, Arock M, Dy M.; Trends Immunol. 2002 May; 23(5):255-63).

Histidine decarboxylase (HDC) is the rate-limiting enzyme in the biosynthesis of histamine (Watanabe T, Yamatodani A, Maeyama K, Wada H: Pharmacology of α-fluoromethylhistidine, a specific inhibitor of histidine decarboxylase. Trends Pharmaceutical Sci 1990; 11:363-367.) Mammalian HDC is a member of a large family of pyridoxal 5-phosphate (PLP)-dependent enzymes (Christen P, Mehta P: From Cofactor to enzymes. The molecular evolution of pyridoxal-5'-phosphate-dependent enzymes. Chemical Record 2001; 1:436-447.) HDC is expressed in most tissues but the highest levels are found in the skin, the GI track and the airways. HDC is a 74 Kd enzyme that is converted to a shorter 54 Kd form (Yatsunami K, Tsuchikawa M, Kamada M, Hori K, Higuchi T: Comparative studies of human recombinant 74- and 54-kDa L-histidine decarboxylase. J. Biol. Chem. 1995; 270: 30813-30817). Both forms are active in vitro but they are not found in the same subcellular compartments; the 74 Kd form being found predominantly in the endoplasmic reticulum (Tanaka S, Nemoto K, Yamamura E, Ohmura S, Ichikawa A: Degradation of the 74 kDa form of l-histidine decarboxylase via the ubiquitin-proteasome pathway in a rat basophilic/mast cell line (RBL-2H3). FEBS Letters 1997; 417:203-207).

The recent generation of HDC-deficient mice provided a good system to study the role of endogenous histamine in a broad range of normal and disease processes (Ohtsu H, Watanabe T: New functions of histamine found in histidine decarboxylase gene knockout mice. Biochem Biophys Res Commun 2003; 443-447). The HDC$^{-/-}$ mice have a reduced number of mast cells and reduced granular content such as mast cell proteases (Ohtsu H, Tanaka S, Terui T, Hori Y, Makabe-Kobayashi Y, Pejler G, Tchougounova E, Hellman L, Gertsenstein M, Hirasawa N, Sakurai E, Buzas E, Kovacs P, Csaba G, Kittel A, Okada M, Hara M, Mar L, Numayama-Tsuruta K, Ishigaki-Suzuki S, Ohuchi K, Ichikawa A, Falus A, Watanabe T, Nagy A: Mice lacking histidine decarboxylase exhibit abnormal mast cells. FEBS 2001; 502:53-56.) These mice show reduced airway hyperresponsiveness (Kozma G T, Losonczy G, Keszei M, Komlosi Z, Buzas E, Pallinger E, Appel J, Szabo T, Magyar P, Falus A, Szalai C: Histamine deficiency in gene-targeted mice strongly reduces antigen-induced airway hyper-responsiveness, eosinophilia and allergen-specific IgE. International Immunol. 2003; 15:963-973, reduced vascular permeability (Ohtsu et al. Plasma extravasation induced by dietary supplemented histamine in histamine-free mice. Eur J. Immunol. 2002; 32:1698-708), reduced skin inflammation (Ghosh A K, Hirasawa N, Ohtsu H, Watanabe T, Ohuchi K: Defective angiogenesis in the inflammatory granulation tissue in histidine decarboxylase-deficient mice but not in mast cell-deficient mice. J. Exp. Med. 2002; 195:973-982.) and increased bone density (Fitzpatrick L A, Buzas E, Gagne T J, Nagy A, Horvath C, Ferencz V, Mester A, Kari B, Ruan M, Falus A, Barsony J. Targeted deletion of histidine decarboxylase gene in mice increases bone formation and protects against ovariectomy-induced bone loss. Proc Natl Acad Sci USA. 2003; 100(10):6027-32). Thus, potent inhibitors of HDC activity might prove useful in allergic, inflammatory, immunological, bone and cardiovascular disorders. Histamine has also been shown to be a positive regulator of proliferation in some types of cancers (Hegyesi H, Somlai B, Varga V L, Toth G, Kovacs P, Molnar E L, Laszlo V, Karpati S, Rivera E, Falus A, Darvas Z. Suppression of melanoma cell proliferation by histidine decarboxylase specific antisense oligonucleotides. J Invest Dermatol. 2001 July; 117(1):151-3).

The biological role of histamine has been extensively studied with pharmacological approaches using histamine receptor specific agonists or antagonists. Despite the important role of HDC in allergic and inflammatory responses, very few small molecule inhibitors of this enzyme are known. Most of these inhibitors were discovered by rational design strategies and are histidine analogues. A well characterized HDC inhibitor is the irreversible inhibitor alpha-fluoromethyl histidine (Watanabe T, Yamatodani A, Maeyama K, Wada H. Pharmacology of alpha-fluoromethylhistidine, a specific inhibitor of histidine decarboxylase. Trends Pharmacol Sci. 1990 11:363-7).

The ability to identify novel classes of HDC inhibitors is limited by the lack of assays that are suitable to HTS. The most commonly used assay to measure HDC activity is based on the o-phthalaldehyde (OPT) method (Roskoski R, Roskoski L M: A rapid histidine decarboxylase assay. Analytical Biochem. 1978; 87:293-297.) This assay is not selective for histamine over histidine and involves a chromatographic separation of the enzyme product from the substrate. Another more sensitive HDC assay utilizes the conversion of [14C]-labeled histidine to [14C]-labeled-histamine. Thin layer chromatography is then used to resolve substrate and product. Histamine ELISA kits could potentially be adapted to measure HDC activity. However, these assays require an acetylation step (acetylated histamine) to reach any useful selectivity and sensitivity. Moreover, these procedures require many washing steps rendering them less amenable for HTS.

BRIEF SUMMARY OF THE INVENTION

A fluorescence polarization assay for determining the HDC modulating activity of a candidate compound comprising the steps of:

a) providing a reaction mixture comprising HDC, histidine, a fluorescently labeled histamine probe, a candidate compound and an anti histamine antibody having selectivity for histamine at least 10 fold greater than histidine;
b) incubating the reaction mixture;
c) determining whether inhibition of HDC has occurred in the presence of the test compound, wherein an increase in fluorescence polarization signal is an indication that the test compound inhibits the activity of the HDC.

In another embodiment of the invention the anti histamine antibody has a selectivity for histamine of at least 100 fold greater than histidine.

In another embodiment of the invention the reaction mixture is incubated for more than 15 minutes and more preferable for between 60 and 120 minutes and most preferably for between about 80 to 100 minutes.

In another embodiment of the invention uses a human HDC.

In another embodiment of the invention the HDC is a recombinant enzyme or alternatively partially purified.

In another embodiment of the invention the histamine probe has an affinity of greater than 1 μm for the anti histamine antibody.

In another embodiment of the invention the antihistamine antibody used is generated by immunizing mice with a histamine bridged by a linker region to a carrier and where said linker is structurally homologous to the fluorescein probe.

In another embodiment of the invention the linker region is 1,4-benzoquinone and the carrier is albumin.

In another embodiment of the invention the fluorescently labeled histamine probe is chosen from FITC, rhodamine, TAMRA, or Cy5.

In another embodiment of the invention the histidine concentration is between 10 μM to 5 mM and more preferably between 100 μm and 1 mM.

Another aspect of the invention provides a method for detection of HDC activity in a patient sample as a diagnostic tool for a disease, wherein said method comprises:
a) contacting said sample with a reaction mixture comprising a HDC, histidine, a fluorescently labeled histamine probe and an anti histamine antibody having selectivity for histamine at least 10 fold greater than histidine;
b) incubating the reaction mixture;
c) determining whether an increase in HDC activity has occurred in the patient sample compared to the level of HDC activity in control sample, wherein a decrease in fluorescence polarization signal relative to the control sample is an indication that the patient sample is at risk for the disease.

In another embodiment of the invention the antihistamine antibody used is generated by immunizing mice with histamine bridged by a linker region to a carrier wherein said linker is structurally homologous to the histamine-fluorescein probe.

In another embodiment of the invention the disease is chosen from cancer, asthma and mastocytoma, immunological disorders, and gastrointestinal disorders.

BRIEF DESCRIPTION OF THE DRAWINGS

FIG. 3 shows the displacement of FITC-histamine binding to the anti-histamine antibody by histamine (●) or histidine (□). Triplicate determinations in a 96-well plate were performed as described in the Methods, with 6 nM FITC-histamine, 50 nM anti-histamine antibody, and the indicated concentration of competitor ligand.

DETAILED DESCRIPTION OF THE INVENTION

Figure 1A:
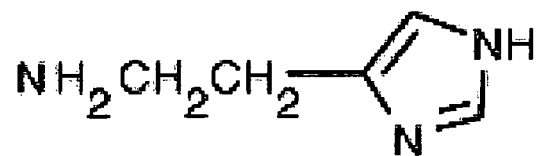
FIG. 1A shows the structure of histamine.

Florescent labeled histamine probe. The present invention provides for a fluorescent probe. The preferred probe is FITC-Histamine (Thiourea, N-[3',6'dihydroxy-3-oxospiro[isobenzofuran-1 (3H), 9'-[9H]xanthene-5(or 6-yl)-N'-[2-(1H-imidazol-4-yl)ethyl]-2,4-dimethyl-, disodium salt) which can be obtained from Molecular Probes (Eugene, Oreg.). Other suitable probes include histamine labeled with rhodamine, TAMRA, or Cy5.

Anti-histamine antibodies. The present invention provides an assay that uses anti histamine antibodies. One suitable monoclonal antibody that can be used is histamine antibody D22.12 which can be obtained from Argene (Varilhes, France). The D22.12 antibody was generated by immunizing mice with 2-histaminyl-1,4-benzoquinone coupled to albumin (Guesdon J L, Chevrier D, Mazie J C, David B, Avrameas S: Monoclonal anti-histamine antibody. Preparation, characterization and application to enzyme immunoassay of histamine. J. Immunol. Methods 1986; 87:69-78.) whereas all the other antibodies we tested were generated by immunization with histamine or acetylated histamine coupled to albumin. The high binding affinity of D22.12 for histamine-fluorescein could result from a structural homology between the immunogen used to obtain D22.12 (histaminyl benzoquinone) and the histamine-fluorescein probe. Other antihistamine antibodies suitable for use in the invention could be generated using immunogens with similar linkers that also have structural homology to the histamine probe. Different anti-histamine antibodies may be used depending on the fluorophore used as a probe.

Histidine can be obtained from Sigma Chemical Co. (St. Louis, Mo.).

Source of HDC Enzyme a) Recombinant—In the preferred embodiment of the invention the human HDC enzyme is used. It is contemplated that either the full length protein be used or a truncated form such as the 53 KD form can be used so long as the truncated form retains the histidine decarboxylase activity. Preferably, the human HDC protein (SEQ ID. 1) or a fragment thereof is used. The HDC protein can also be fused to protein tags, such as glutathione S-transferase (GST), to facilitate the purification.

b) Purified—The method of the invention can be practiced using a purified HDC enzyme. As used in the text herein the term partially purified is meant to include a HDC enzyme that has been partially purified to a greater extent than the HDC enzyme would be found in the human cell. Purification procedures for HDC are known in the art and are taught by Watabe A, Fukui T, Ohmori E, Ichikawa A: Purification and properties of L-histidine decarboxylase from mouse stomach. Biochem. Pharmacol. 1992; 43:587-593 the contents of which are incorporated herein.

Standard Assay for Detecting Inhibitors

In the standard assay, HDC, diluted in a HDC buffer containing a reducing agent such as DTT and the enzyme co-factor PLP, is added to a sample plate. A test compound in HDC Buffer plus a suitable amount of DMSO or buffer alone is added to the plate. Fluorescently labeled-histamine and histidine are combined in FP Buffer and transferred to the plate in 10 µL. Finally, 90 nM anti-histamine antibody is added in 20 µL of FP Buffer. Thus, the final concentrations in the assay are: HDC 25 to 50 nM, FITC-histidine 3 to 6 nM, histidine 300 to 600 uM, anti-histamine antibody 25 to 50 nM, and DMSO 1 to 5%. The plate is then incubated at 37° C. for at least 15 minutes. The fluorescence polarization signal is read on a suitable intstrument for reading fluorescence polarization such as an LJL Analyst (Molecular Devices, Sunnyvale, Calif.) with excitation at 485 nm, emission at 530 nm, a fluorescein dichroic mirror at 505 nm and G factor set to 1. A decrease in fluorescence signal is an indication that the test compound inhibits the activity of the HDC.

Modifications of Standard Procedure for Detecting Candidate Inhibitors—

Optimization of Parameters

The present invention provides an HDC assay for determining HDC modulating activity of a candidate compound and a diagnostic method for determining HDC levels in patient samples. It is contemplated that a person skilled in the art may practice the invention in a manner in which a number of parameters may be altered in order to adapt the assay for their own use. Some of the parameters that may be altered include: the anti-histamine antibody concentration, the concentration of the substrate histidine, the probe concentration, the source and concentration of the HDC enzyme, the test compound concentration, the order of additions of the components, the volume of the individual components, the total volume of reaction, addition of a pre-incubation step of HDC with the test compound before the reaction, the duration of the reaction, the temperature of the reaction, the type of assay plates, a cooling or heating step, addition of a step to stop the enzymatic reaction (ex: acid, base, salt, known HDC inhibitors or else), the type of instrument and related parameters used to read the fluorescence polarization signal.

Selectivity of the Fluorescent Probe for its Receptor Target Molecule.

In one embodiment of the invention the selectivity of the anti-histamine antibody for histamine over histidine is greater than 100×. A suitable candidate inhibitor would be expected to have an IC50 of <10 µm.

Standard Assay for Diagnosing Diseases

Methods to extract and prepare tissues or serum from normal or diseased samples to measure HDC activity are known in the art. For example: (1)1—Sieja K, Stanosz S, von Mach-Szczypinski J, Olewniczak S, Stanosz M. Concentration of histamine in serum and tissues of the primary ductal breast cancers in women. Breast. 2005 June; 14(3):236-41; (2) E. Masini, V. Fabbroni, L. Giannini, A. Vannaccil, L. Messerini, F. Perna, C. Cortesini and F. Cianchi Histamine and histidine decarboxylase up-regulation in colorectal cancer: correlation with tumor stage Inflamm. res. 54, *Supplement* 1 (2005) S80-S81; (3) 3-Fogel W A, Dudkowska M, Wagner W, Grzelakowska-Sztabert B, Manteuffel-Cymborowska M. Ornithine and histidine decarboxylase: activities in hypertrophic and hyperplastic mouse kidney. Inflamm Res. 2005 April; 54 Suppl 1:S62-3.

These methods could be applied to prepare samples for testing in the fluorescent HDC assay described herein. Our method would allow for high throughput testing of HDC activity in the target normal or diseased tissue or plasma or blood samples.

EXAMPLES

Reagents

FITC-Histamine (Thiourea, N-[3',6'dihydroxy-3-oxospiro [isobenzofuran-1 (3H), 9'-[9H]xanthene-5(or 6-yl)-N'-[2-(1H-imidazol-4-yl)ethyl]-2,4-dimethyl-, disodium salt) was obtained from Molecular Probes (Eugene, Oreg.). Histamine monoclonal antibody 22.12 was obtained from Argene (Varilhes, France). L-Histidine, histamine, potassium phosphate (1M mono- and dibasic solutions), polyethylene glycol 400 molecular weight, ethylene glycol tetraacetic acid (EGTA), dithiothreitol, pyridoxal-5-phosphate, and sodium chloride were from Sigma Chemical Co. (St. Louis, Mo.). 3-[(3-Cholamidopropyl)dimethylammonio]-1-propanesulfonate (CHAPS) was obtained from Pierce Chemical Co. (Rockford, Ill.). Dimethylsulfoxide was from Baker Chemical Corp. Black opaque polystyrene 384-well plates were obtained from Coning-Costar. The known HDC inhibitors, histidine-methyl ester, and His-Phe were from Sigma Chemical Co and alpha-fluoromethylhistidine was obtained from the Boehringer Ingelheim Pharmaceuticals compound library.

Buffers

HDC Buffer is comprised of 200 mM potassium phosphate (pH 6.8), 2% PEG-400, 0.2 mM EGTA, and 0.03% CHAPS. FP Buffer is 16.6 mM Tris-HCl (pH 7.5) and 50 mM NaCl.

HPLC Determination of Histamine Content

HPLC separations were performed on an Agilent 1090M equipped with a diode array detector. A Delta-Pak HPI C4 300 Å, 2.0×150 mm column (Waters) was used. The mobile phase consisted of 20 ml PIC® B-8 Low UV Reagent (Waters) in 1000 ml 10 mM triethylamine phosphate, pH 3.0. All separations were carried out at room temperature (22° C.) with a flow rate of 0.2 ml/min and were monitored at a wavelength of 215 nm.

Histamine concentrations were calculated using standard curves for concentration vs. area response. The standard curves were generated using duplicate injections of histamine in control buffer at concentrations of 0 to 200 or 600 µM. Six equally spaced concentrations were used. The standard curves were calculated for concentration in µvs. area response using linear regression on a TI-68 calculator. Correlation coefficients were greater than 0.999.

Cloning of Human HDC

The cDNA corresponding to the truncated 53 Kd form of full length human HDC (accession number: NM_002112) was amplified by PCR using total RINA from the human mast cell line HMC-1 (Maeda K, Taniguchi H, Ohno I, Ohtsu H, Yamauchi K, Sakurai E, Tanno Y, Butterfield J H, Watanabe T, Shirato K: Induction of L-histidine decarboxylase in a human mast cell line, HMC-1. *Exp Hematol.* 1998; 26:325-3 1.). The primers used were: 5'-atgatggagcctgaggagtacagag (SEQ ID NO: 2) and 3'-acactactgactcaggatgagagt (SEQ ID NO: 3). The HDC cDNA (1.5 Kb) was cloned into the pcDNA4.1 vector. Clone pcDNA 4.1-HDC was used as template to obtain a PCR product containing the first 1431 bases (amino acid residues 1-477) of HDC and incorporating a thrombin cleavage site 5' and adjacent to the first base. This PCR product was cloned into pDEST 20 using Gateway Cloning Technology (Invitrogen Life Technologies) following the manufacturer's protocols. DNA purified from the final expression clone was sequenced confirmed and then transformed into DH10Bac *E. coli* for transposition into the bacmid. Recombinant bacmid DNA was purified from single colonies and transposition was verified by PCR analysis.

Baculoviral Expression and Purification of GST-HDC

A 20 L volume of SF900II-SFM (Invitrogen cat# 10902-088) was sterile filtered into a 30 L MBR stirred tank bioreactors. The MBR bioreactor was equipped with pH, dissolved oxygen and temperature probes and control set points were: pH 6.2, DO 50%, Temp 27° C., RPM 110. Four 1 L shake flasks of Sf9 cells were grown to a cell density between $2.5 \times 10^6$ and $3 \times 10^6$ cells/mL and were used to inoculate the bioreactor, resulting in 24 L of media with an approximate cell density of $4 \times 10^5$ to $5 \times 10^5$ cells/mL. The inoculated bioreactor was sampled daily for cell density, viability, and cell diameter using a Cedex cell counter (Innovatious). Nutrient (glucose, glutamine) and waste (ammonia) analysis was also carried out daily using a Bioprofile 100 analyzer (Nova Biomedical). Twenty-four hours after the initial cell inoculation, the bioreactor was infected with GST-HDC baculovirus to achieve an MOI of 0.1. A 1.5 mL cell supernatant sample (centrifuged, decanted and frozen) was taken pre-infection and every 24 hours until the run was harvested for SDS-PAGE and WESTERN analysis. Twenty-four hours after infection, 25 mg of Leupeptin was dissolved in SF900II-SFM media, filter sterilized and injected into the bioreactor. Runs were harvested 48 hours post-infection. The infected cells were pelleted in a 12 L centrifuge (Sorvall BP12)@ 3000 rpm, 4° C. for 10 min per spin. The pellets were the combined into one centrifuge bottle and given a final spin at 3500 rpm for 10 minutes, at 4° C. Pellets were weighted and frozen at −80° C. until use. The standard pellet yield was 300 grams.

For protein purification, all buffers were prepared from distilled and deionized water and all procedures were carried out at 4° C. The cell pellet was mixed with lysis buffer (20 mM Hepes, pH 7.5, 150 mM KCl, 10% glycerol, 2 mM DTT, 1 mM EGTA, Roche protease inhibitor cocktail tablets, and 0.01 mM PLP) at a ratio of 5 ml/g of cell pellet. The cells were homogenized on ice using PolyTron PT 2100 (Kinematica AG, Switzerland), then sonicated 3 times for 5 min with a Branson Sonifier 450 (Converter, USA) at 50% duty cycle. The cell lysate was centrifuged at 18,600 g for 30 min followed by 225,071 g for 60 min. The clarified lysate was loaded directly onto a 50 mL Glutahione SEPHAROSE® 4B column (Amersham, Sweden) using a AKTA Prime chromatography system (Amersham, Sweden). After loading, the column was washed with 4 column volumes (CV) of wash buffer (20 mM Hepes, pH 7.5, 150 mM KCl, 10% Glycerol, 2 mM DTT, 0.5 mM EDTA, 0.5 mM PMSF and 0.01 mM PLP), then was eluted with 10 CV of elution buffer (20 mM GTH reduced, 2 mM DTT and wash buffer, pH 8.0). The HDC product eluting from the column was pooled according to visual inspection of an SDS-PAGE gel. A standard yield was 33 mL of HDC at 1.8 mg/mL. The pooled product was dialyzed into 5 L of buffer 1 (20 mM Hepes, pH 7.5, 0.1 mM EGTA, 0.2 mM PMSF, 0.25 mM DTT, 10% Glycerol and 0.01 mM PLP) for 4 hours, then dialysis into 5 L of buffer 2 (0.1 M K Phosphate, pH 7.5, 2% PEG-400, 0.1 mM EGTA, 2 mM PMSF, 10% Glycerol and 0.02 mM PLP) for 17 hours. The final product was aliquoted, snap frozen in liquid nitrogen, and stored at −80° C.

Histidine Decarboxylase Assay

In the standard assay, HDC, diluted to 90 nM in HDC Buffer plus 0.9 mM DTT and 99 µM PLP, was added to a black opaque 384-well plate in 20 µL. Test compound in HDC Buffer plus 6% DMSO or buffer alone was added to the plate in 10 µL. 36 nM FITC-histidine and 3.6 mM histidine were combined in FP Buffer and transferred to the plate in 10 µL. Finally, 90 nM anti-histidine antibody was added in 20 µL of FP Buffer. Thus, the final concentrations in the assay were: HDC 30 nM, FITC-histidine 6 nM, histidine 600 µM, anti-histamine antibody 30 nM, DMSO 1%. The plate was incubated at 37° C. for 90 minutes. The fluorescence polarization signal was read on an LJL Analyst (Molecular Devices, Sunnyvale, Calif.) with excitation at 485 nm, emission at 530 nm, a fluorescein dichroic mirror at 505 nm and G factor set to 1. A 96-well plate version of the assay, used in assay development, was performed as described above with twice the volumes indicated for 384-well plates.

High Throughput Screening

The assay was automated on a Zymark Allegro™ robotics system (Caliper-Zymark, Hopkinton, Mass.), using a Multidrop to add enzyme, the Sciclone to add substrate/probe and test compound, and a Multidrop to add the antibody. The plates were incubated at 37° C. in a humidified environment, and fluorescence polarization was read on an LJL Analyst integrated into the Allegro system using the settings described above. Compounds were screened at a concentration of 5 µg/mL. The POC values were calculated relative to an assay blank containing complete reaction minus HDC, and a 100% control containing HDC buffer with 1% DMSO in place of compound.

Results

Figure 1B:
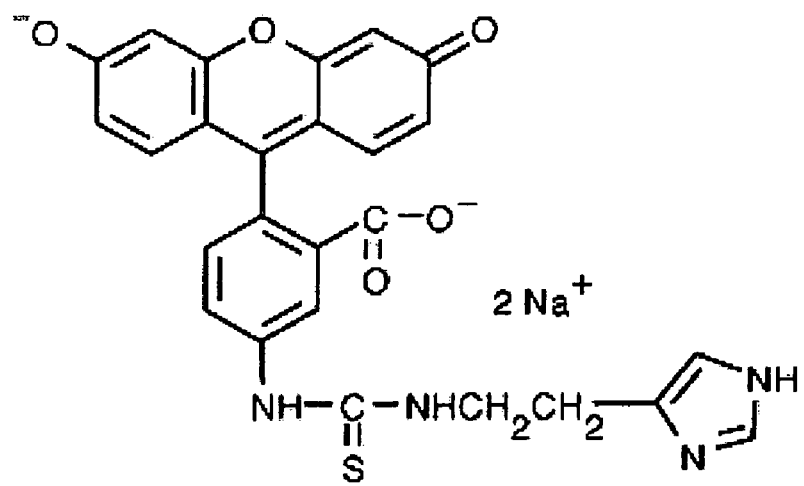
FIG. 1B shows the structure of N-[3',6'-dihydroxy-3-oxospiro[isobenzofuran-[(3H), 9'-[9H]xanthene-5(or 6)-yl]-N'-[2-(1H-imidazol-4-yl)ethyl]-2,4-dimethylthiourea, disodium salt (FITC-histamine) the probe molecule.

The structure of the HDC enzyme product (histamine) and the histamine probe (FITC-histamine) are shown in FIG. 1. We first set out to examine the interaction of several commercial anti-histamine antibodies to the FITC-histamine probe (data not shown). One of these antibodies (D22.12), showed strong probe binding as measured by fluorescence polarization and was retained for further characterization.

Figure 2:
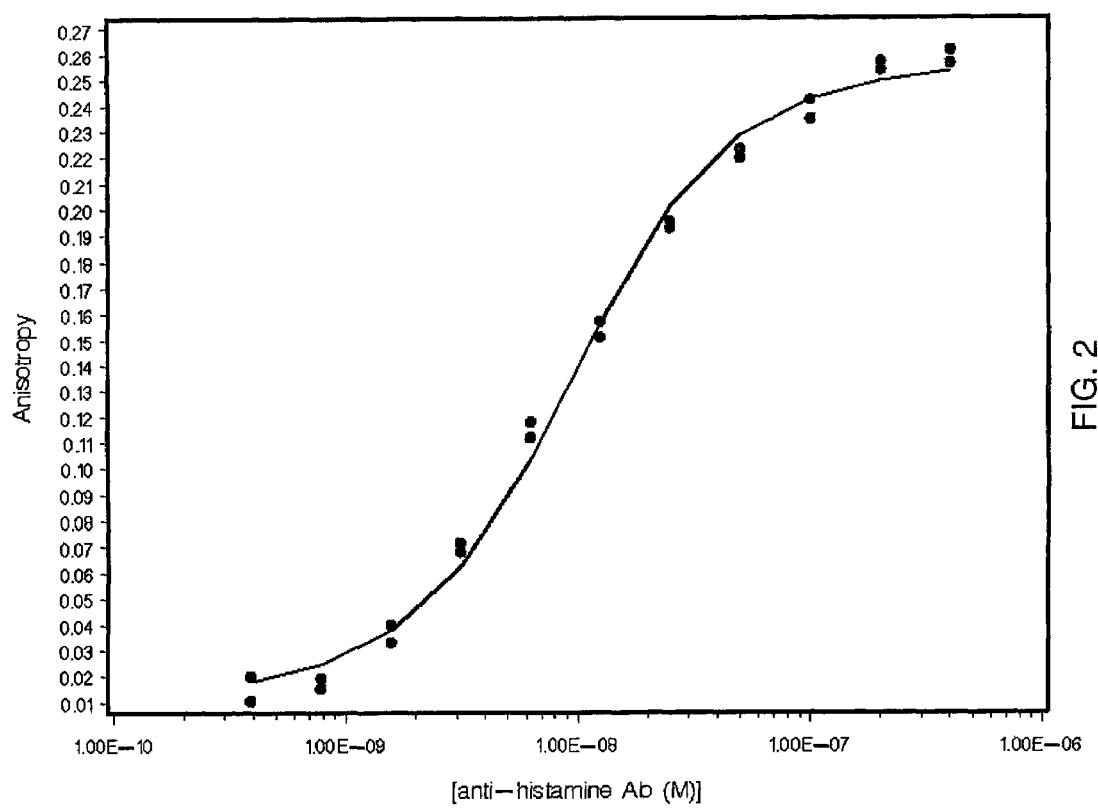
FIG. 2 shows the binding of FITC-histamine to the anti-histamine antibody. The assay was run in duplicate in a 96-well plate as described in the Methods, with FITC-histamine at 6 nM. The data was fit in SAS and a Kd of 3.9 nM was determined.

We first determined the affinity of the probe for the antibody and the specificity of the interaction, both of which are crucial to constructing a robust assay in a competitive mode. FIG. 2 shows a binding curve of probe and antibody as determined by measurement of anisotropy. The probe concentration was held at 6 nM and the antibody concentration varied over approximately 3 logs. A dissociation constant of 3.9 nM was determined upon fitting the data. The specificity of the antibody for histamine over histidine was demonstrated as shown in FIG. 3. Probe and antibody concentrations were held constant at 6 and 50 nM, respectively, while the concentrations of histamine and histidine were varied as shown. Histidine was unable to compete with FITC-histamine for binding to the antibody over the 5 log range examined. Histamine, however, freely competed with the probe for antibody binding, yielding an IC50 of 135 µM. Thus, the tight and specific binding of FITC-histamine to the histamine monoclonal antibody and the ability to compete for that binding with the product of the enzymatic reaction suggests that it is possible to develop a robust competitive FP assay for HDC.

Figure 4A:
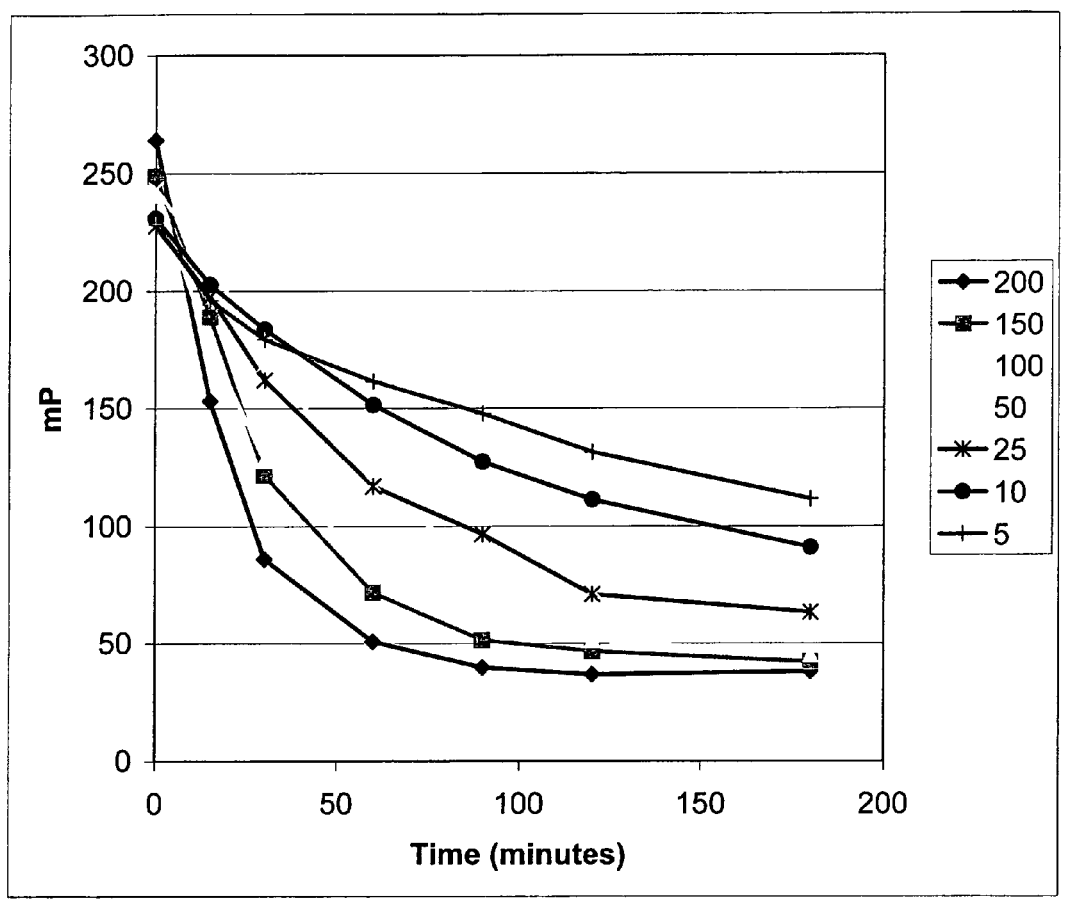
FIG. 4A shows a time course of HDC at various enzyme concentrations. Triplicate reactions in a 384-well plate were initiated by the addition of the indicated concentration of HDC, and fluorescence polarization was determined at time points from 0 to 180 minutes of incubation. Probe, substrate, and antibody concentrations were as described in the standard assay.
Figure 4B:
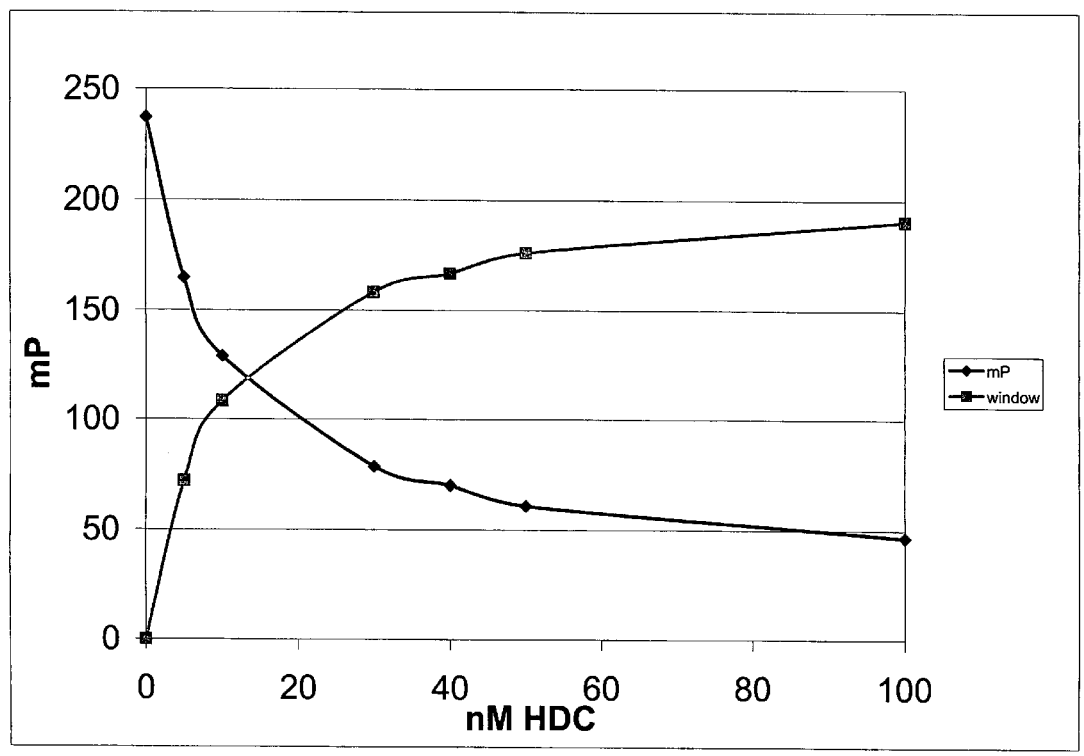
FIG. 4B. HDC titration at 90 minutes. Assays (384-well) were performed in quadruplicate using the indicated concentration of HDC for 90 minutes at 37° C. on the Allegro™ system. The assay window is defined as the difference in mP between the blank (no enzyme) and reaction wells.

FIG. 4A shows a time course of the enzymatic reaction at various concentrations of HDC. Histidine, at 600 uM, was approximately twice the reported Km of 200-400 uM (Watabe et al 1992). At HDC concentrations >100 nM, the reaction is linear for only about 30 minutes. In order to balance the size of the assay window with the enzyme requirements for a large scale screen and linearity of the reaction, we chose to use 25-50 nM HDC and an incubation time of 90 minutes in the standard assay. This was further refined in FIG. 4B, which shows a titration of HDC at a 90 minutes incubation performed on the Allegro robotic system. From this experiment we arrived at an enzyme concentration of 30 nM. Thus, the final assay conditions were set at 30 nM HDC, 30 nM antibody, and 6 nM FITC-histamine in a total volume of 60 µL for 90 minutes at 37° C. The PLP concentration was set at 33 µM to maintain saturation of the enzyme.

Figure 5:
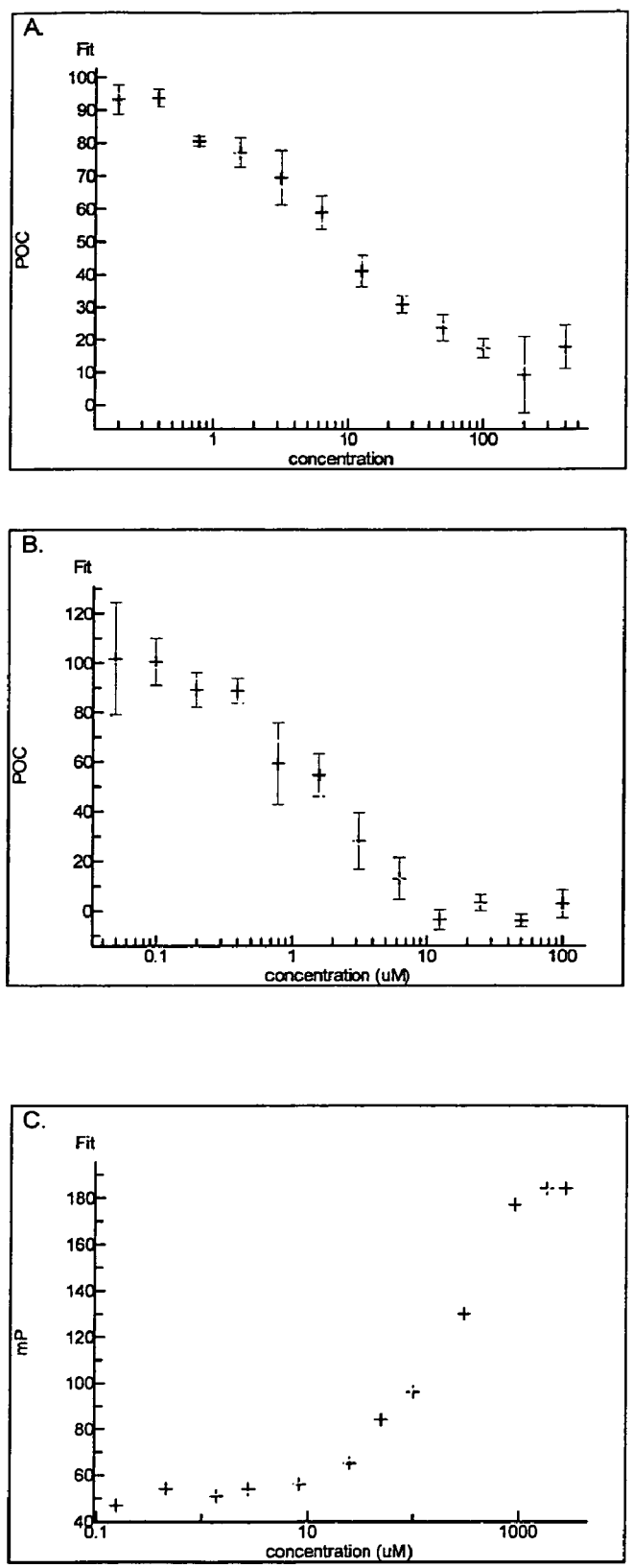
FIG. 5 shows the inhibition of HDC by methyl ester histidine (A), α-fluoromethylhistidine (B), and the dipeptide histidine-phenylalanine (C). Reactions were run using the standard conditions as described in the Methods and the indicated concentration of inhibitor. IC50 values were obtained by fitting the data using XLFit4 (IDBS Software). Error bars show the mean±S>D of triplicate determinations.

FIG. 5 shows the behavior of 3 known HDC inhibitors: methyl ester histidine, α-fluoromethyl histidine, and the dipeptide histidine-phenylalanine in the standard assay. We determined IC50's of 7.7 uM, 1.4 uM, and 228.1 uM for the 3 compounds, respectively. These values are in good agreement with those obtained using the HPLC assay.

Figure 6:
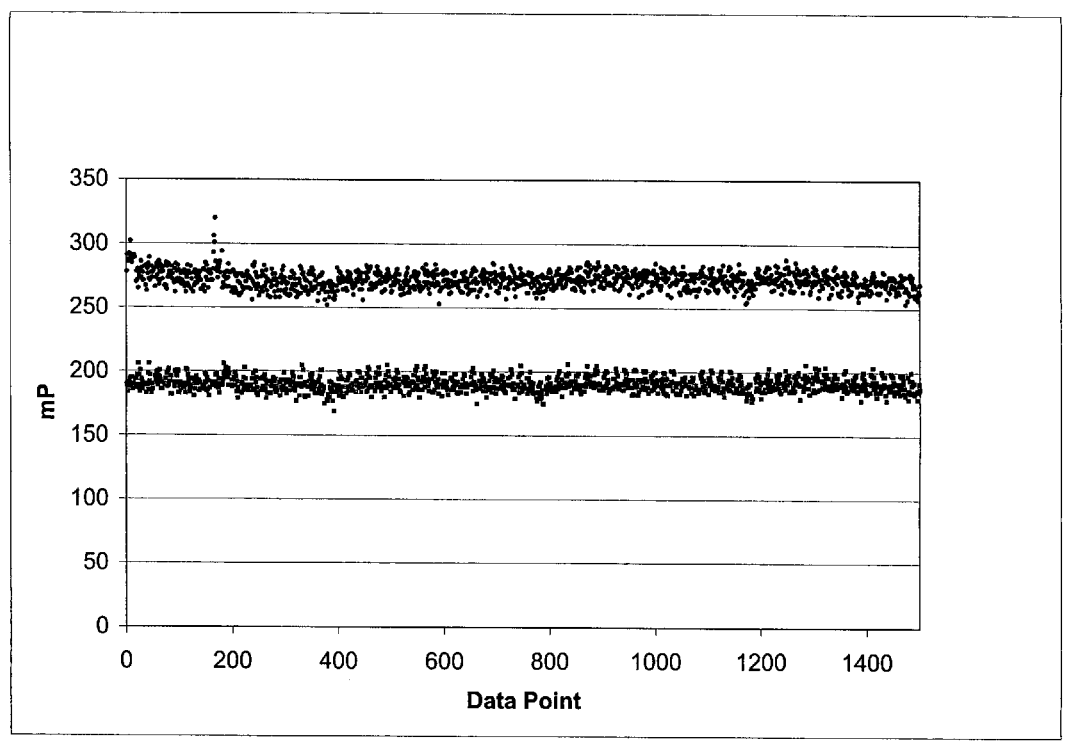
FIG. 6 shows the scatter plot of blank (•) and positive control (□) values from a single day's screening run of 90 plates (384 wells).

The assay as described was then used to screen compounds from a library at a final concentration of 5 µg/mL. 384-Well plates were set up to contain 352 compound wells, 16 control wells (no compound) and 16 blank wells (no enzyme) per plate. Compounds, in neat DMSO, were diluted in buffer to give a final DMSO concentration of 1% in the assay. This concentration of DMSO was shown to have no effect on the enzymatic activity or stability (data not shown). The assay was fully automated on the Allegro robotic system, enabling throughputs of approximately 100 plates per day. FIG. 6 shows a scatter plot of blank and control wells for a single screening run of 90 plates, with an average Z' of 0.6 and an assay window of 80-100 mP. In excess of 600,000 compounds were screened in the assay with a confirmed hit rate of 0.05% using 60% of control as the hit criteria. Confirmed hits were subsequently assayed in 10 point dose response to assess potency.

Discussion

An important parameter contributing to the performance of an FP assay is the affinity of the fluorescent probe for its receptor or target molecule. As a general rule, the Kd for probe binding to its receptor is inversely proportional to the fraction bound. Thus, high affinity binding allows for an optimal fluorescent-ligand/receptor stoichiometry and a robust FP signal. We screened multiple anti-histamine antibodies in order to find one that had a suitable affinity for our histamine-fluorescein probe. Only one of these antibodies, D22.12, had an affinity that was high enough for the development of an FP assay. The D22.12 antibody was generated by immunizing mice with 2-histaminyl-1,4-benzoquinone coupled to albumin (Guesdon et al; 1986) whereas all the other antibodies we tested were generated by immunization with histamine or acetylated histamine coupled to albumin.

The high binding affinity of D22.12 for histamine-fluorescein could result from a structural homology between the immunogen used to obtain D22.12 (histaminyl benzoquinone) and the histamine-fluorescein probe.

The Km of HDC (54 Kd form) for its substrate histidine is 275 µM (data no shown). Thus, an important requirement for the development of an HDC assay is the selectivity for histamine over histidine. Our FP assay shows over a 100-fold selectivity for histamine over histidine. However, as shown in FIG. 3, the histidine concentration should be kept below 2 mM due to non-specific increase in the FP signal. This limitation should not be an issue in most applications to measure HDC activity given that the Km of the enzyme is much lower than the maximal amount of histidine tolerated by the assay.

Decarboxylases form a large family of enzymes playing important physiological roles (Christen et al; 2001). For example, DOPA decarboxylase is responsible for the synthesis of the key neurotransmitters dopamine and serotonin via decarboxylation of L-3,4-dihydroxyphenylalanine (L-DOPA) and L-5-hydroxytryptophan respectively. Current methods used to measure transmitters such as serotonin and dopamine are analogous the histamine detection techniques. Thus, the assay we describe here for HDC could be applied to related enzymes such as dopa decarboxylase and allow for the development of new inhibitors with better pharmacological characteristic.

The invention claimed is:

1. A fluorescence polarization assay for determining the histidine decarboxylase (HDC) inhibiting activity of a candidate compound comprising the steps of:
   a) providing a reaction mixture comprising a HDC, histidine, a fluorescently labeled histamine probe, a candidate compound and an anti histamine antibody having selectivity for histamine at least 10 fold greater than histidine;
   b) incubating the reaction mixture;
   c) determining whether inhibition of HDC has occurred in the presence of the candidate compound, wherein an increase in fluorescence polarization signal relative to a reference fluorescence polarization signal is an indication that the candidate compound inhibits the activity of the HDC,
   wherein said HDC comprises the polypeptide of SEQ ID. No. 1.

2. The fluorescence polarization assay of claim 1, wherein the anti histamine antibody has a selectivity for histamine of at least 100 fold greater than histidine.

3. The fluorescence polarization assay of claim 1, wherein the reaction mixture is incubated for 15 to 180 minutes.

4. The fluorescence polarization assay of claim 3, wherein the reaction mixture is incubated for between 60 and 120 minutes.

5. The fluorescence polarization assay of claim 4, wherein the reaction mixture is incubated for about 80 to 100 minutes.

6. The fluorescence polarization assay of claim 1, wherein the HDC is a recombinant enzyme.

7. The fluorescence polarization assay of claim 1, wherein the HDC is partially purified.

8. The fluorescence polarization assay of claim 1, wherein the histamine probe has a greater affinity than 1 μm for the anti histamine antibody.

9. The fluorescence polarization assay of claim 1, wherein the antihistamine antibody used is generated by immunizing mice with a histamine bridged by a linker region to a carrier and where said linker is structurally homologous to the fluorescein probe.

10. The fluorescence polarization assay of claim 9, wherein the linker region is 1,4-benzoquinone coupled to a carrier.

11. The fluorescence polarization assay of claim 9, wherein said carrier is albumin.

12. The fluorescence polarization assay of claim 1, wherein the fluorescently labeled histamine probe is chosen from the group consisting of FITC, rhodamine, tetramethylrhodamine and Cy5.

13. The fluorescence polarization assay of claim 1, wherein the histidine concentration is between 10 μM to 5 mM.

14. The fluorescence polarization assay of claim 9, wherein histidine concentration is between 100 μM and 1 mM.

15. The fluorescence polarization assay of claim 1, wherein the reference fluorescence polarization signal is determined by:
   d) providing a reference mixture comprising the fluorescently labeled histamine probe and the anti histamine antibody;

e) incubating the reference mixture; and f) measuring the fluorescence polarization signal of the reference mixture, wherein the measured signal is the reference fluorescence polarization signal.

16. A fluorescence polarization (FP) assay for determining the histidine decarboxylase (HDC) inhibiting activity of a candidate compound comprising the steps of:

a) providing a reaction mixture comprising a HDC comprising the polypeptide of SEQ ID No. 1, histidine, a fluorescently labeled histamine probe, a candidate compound and an anti histamine antibody having selectivity for histamine at least 10 fold greater than histidine;

b) incubating the reaction mixture for a time sufficient to produce histamine but no longer than about 180 minutes;

c) determining the FP signal of the incubated reaction mixture; and d) comparing the FP signal of the incubated reaction mixture with a reference EP signal, wherein if the FP signal of the incubated reaction mixture is about the same as or is greater than the reference FP signal, the candidate compound is an inhibitor of HDC.

17. The fluorescence polarization assay of claim 1, wherein the reaction mixture is incubated for about 30 minutes.

* * * * *